United States Patent [19]

Evans

[11] 4,307,722
[45] Dec. 29, 1981

[54] DILATORS FOR ARTERIAL DILATION

[76] Inventor: Joseph M. Evans, P.O. Box 175, Murrysville, Pa. 15668

[21] Appl. No.: 66,779

[22] Filed: Aug. 14, 1979

[51] Int. Cl.³ .......................................... A61M 29/02
[52] U.S. Cl. .................................... 128/344; 128/341
[58] Field of Search ................................. 128/341, 344

[56] References Cited

U.S. PATENT DOCUMENTS

| | | | |
|---|---|---|---|
| Re. 27,910 | 2/1974 | Birtwell | 128/325 |
| 2,919,697 | 1/1960 | Kim | 128/349 |
| 3,034,510 | 5/1962 | Kittel | 128/344 |
| 3,045,677 | 7/1962 | Wallace | 128/344 |
| 3,504,662 | 4/1970 | Jones | 128/344 |
| 3,834,394 | 9/1974 | Hunter | 128/325 |
| 3,889,685 | 6/1975 | Miller, Jr. et al. | 128/348 |
| 3,991,767 | 11/1976 | Miller, Jr. et al. | 128/348 |
| 4,130,119 | 12/1978 | Sessions et al. | 128/325 |
| 4,143,651 | 3/1979 | Patel | 128/349 B |
| 4,147,169 | 4/1979 | Taylor | 128/349 |
| 4,147,170 | 4/1979 | Taylor | 128/349 |

FOREIGN PATENT DOCUMENTS 15864 10/1912 France ............................... 128/344

OTHER PUBLICATIONS

Journal of Medicine, New England, vol. 301, No. 2, pp. 61–68, Nonoperative Dilation of Coronary-Artery Stenosis, Jul. 12, 1979.

*Primary Examiner*—Norman Yudkoff
*Attorney, Agent, or Firm*—Fleit & Jacobson

[57] ABSTRACT

A dilator, a method of making the dilator, and a method of using the dilator to compress distal end. A second embodiment of the dilator utilizes a tubular member formed by first and second spring wire guides encompassing a plurality of dilating wires surrounding a center pull wire. Near the distal end of the dilator, the spring wire guides are spaced from each other to define a buckling region for the dilating wires. When the center wire is pulled, a compressive force is applied on the dilating wires, so that the wires buckle, or expand, in the buckling region. In one modification of this embodiment, a thin elastic membrane encompasses the dilating wires and the buckling region. In another modification, the thin elastic membrane covers substantially the entire length of the dilating wires so that both pneumatic and mechanical compressive forces can be exerted on the fatty substances. The elastic membrane is positioned inside or on the outside of the spring wire guides. A further embodiment of the dilator utilizes a tubular member having a distal end split by longitudinally-extending slits. Rearward movement of a ball member positioned in front of the leading or distal end of the tubular member, after or simultaneously with rearward movement of a sheath encompassing the split end, forces apart the split end thereby dilating the artery and exerting a compressive force on the fatty substances.

4 Claims, 8 Drawing Figures

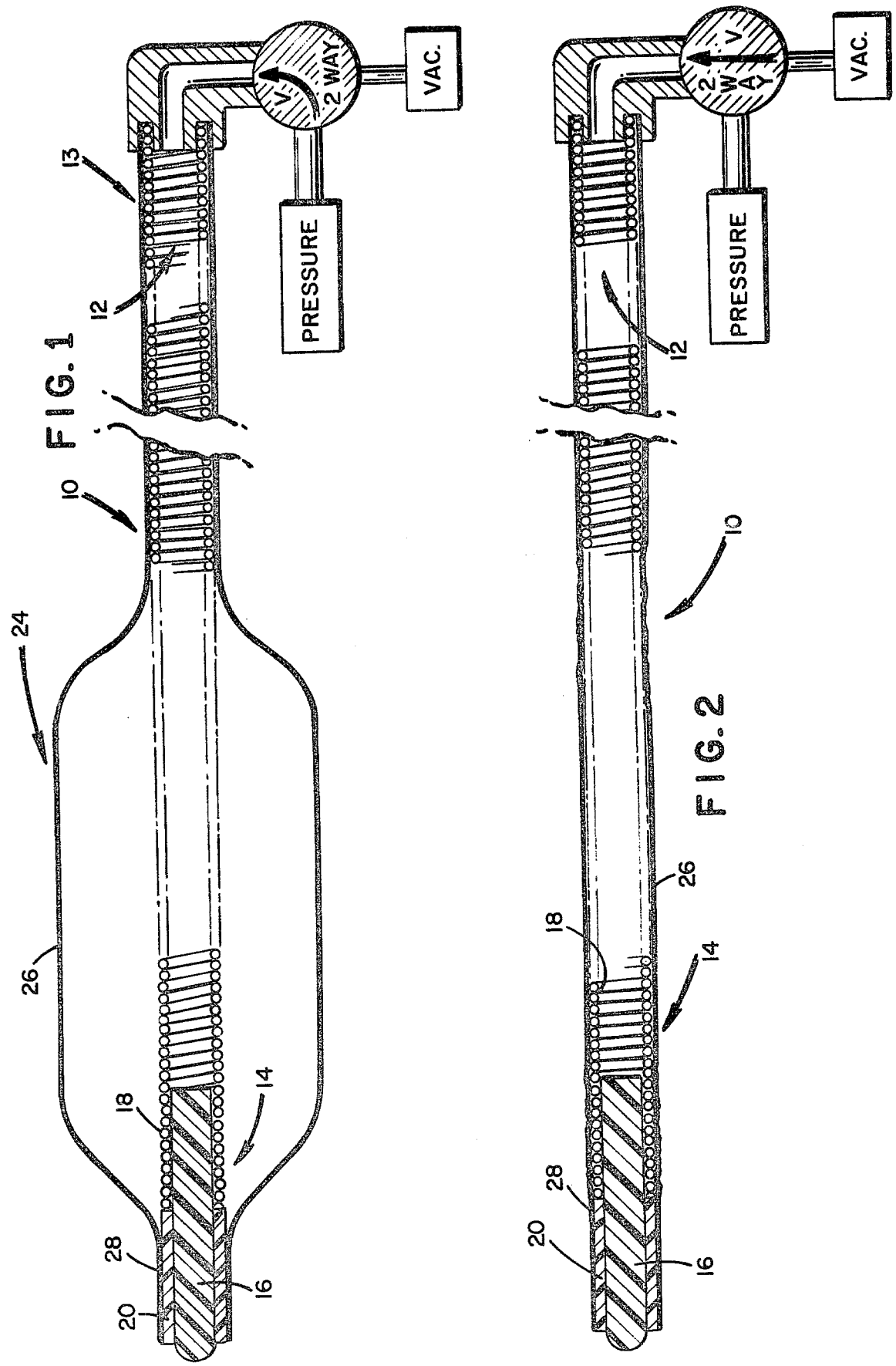

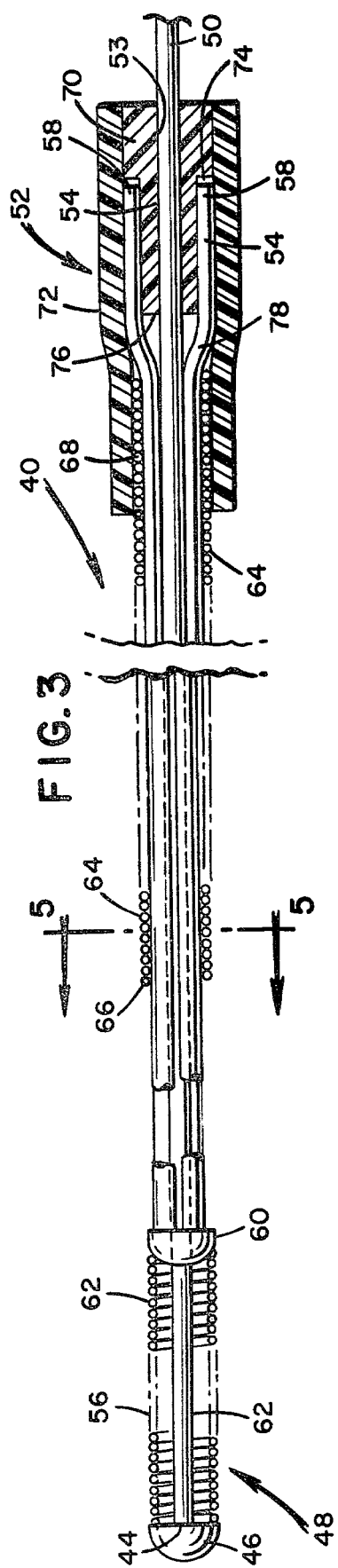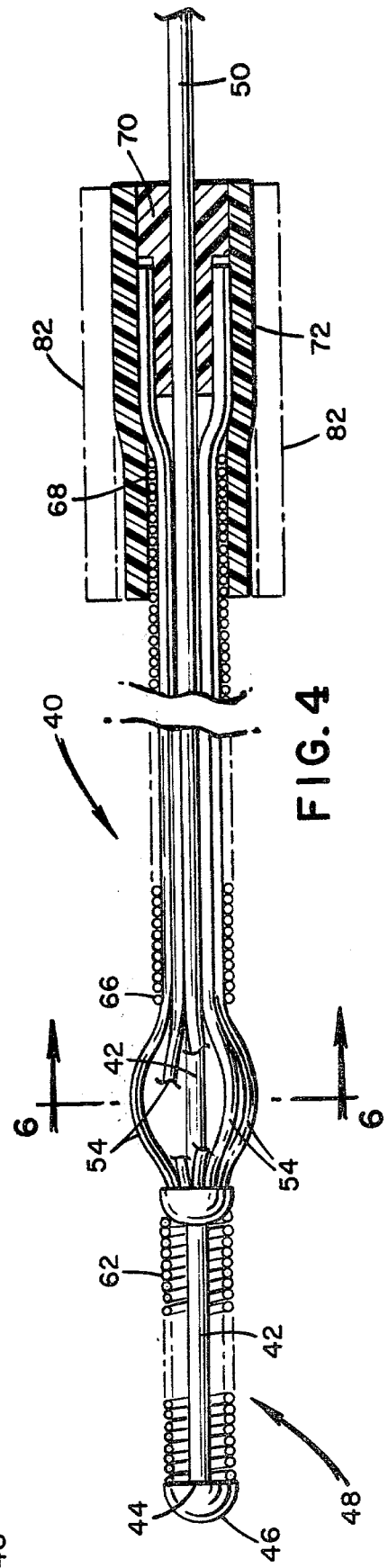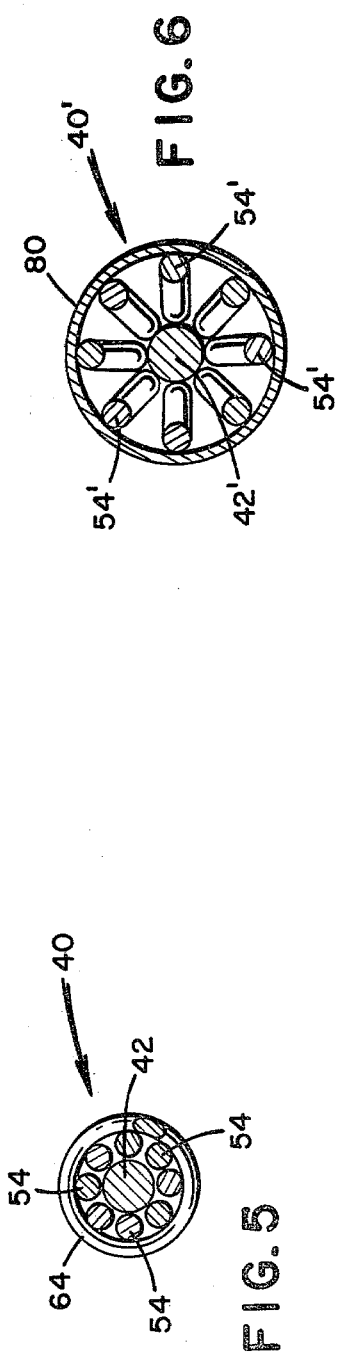

DILATORS FOR ARTERIAL DILATION

BACKGROUND OF THE INVENTION

1. Field of the Invention

The present invention relates to dilators or dilator assemblies for compressing fatty substances deposited in or on the walls and lumen of major arteries.

2. Description of the Prior Art

In our society and in other developed societies, the aging process is accompanied by the deposition of fatty substances in the walls and lumen of the major arteries. The precise causes of this buildup are unknown but are in all likelihood related to diet. The fatty substances are not deposited uniformly throughout the arterial system but, for reasons that are not well understood, are concentrated at various sites within the arteries. These deposits may take the form of hard crystalline masses within the wall of the artery, soft gelatinous masses within the lumen, or various combinations of these conditions. In some instances, these deposits build to such an extent that they severely restrict blood flow to body sites such as the lower extremeties, the brain and the heart.

In cases wherein the deposits have restricted blood flow to such an extent that the individual develops clinical symptoms which indicate that the normal course of life is threatened, the sections of artery which are obstructed by the deposits are removed and replaced with artificial arterial segments or the sections are bypassed using vein segments taken from another site in the body. In either case, the procedure requires a traumatic invasion of the individual's body which is both costly and of high risk.

It has recently been shown by Grunzig that an inelastic sack inserted into the blocked artery can, when properly positioned, be inflated and compress the deposit in the artery. Upon removal of the sack, the deposit remains compressed and the blood flow in the artery is substantially increased.

Since the sack is inserted into the arterial system through a simple incision, for instance, in the groin to reach the femoral artery, the surgical trauma is greatly reduced. Likewise, the risk of the procedure, although still significant, is greatly reduced.

Current methods of fabrication of sacks consist of the joining of a cylindrically shaped sack to the end of a tube which serves as an insertion guide and additionally for transfer of the inflating medium from outside the body to the sack. This device requires two joints, one at each end of the sack. These joints represent potential failure sites, whereby the sack may rupture or separate making the expansion of the sack ineffective and releasing the expansion medium to the bloodstream with increased risk to the individual undergoing the procedure.

Also, indwelling catheters and self-retaining catheters are known that are held in a desired position in a urethra for withdrawal of urine from a bladder. One such catheter is known as the de Pezzer catheter. Such a catheter has a bulbous extremity for holding the catheter in a desired position. Similarly, winged catheters are known that have projections on distal ends of the catheters for retaining them in desired positions.

Further, cannulas, such as Trendelenburg's cannula, are known that have a dilatable rubber bag covering the cannula. Such cannulas are used for closing the trachea to prevent entrance of blood after a tracheotomy.

U.S. patents representative of the aforementioned devices include U.S. Pat. Nos. 2,919,697, 3,834,394, 3,889,685, 3,991,767, 4,130,119, 4,147,169, and Re. 27,910.

SUMMARY OF THE INVENTION

The present invention provides both improved dilators and methods of fabricating and using such dilators. The improved dilators are intended to overcome the problems encountered with use of previously known dilators and similar surgical devices.

One dilator of the present invention eliminates the aforementioned possibility of leakage through joints or rupture of joints connecting a cylindrically shaped sack to an end of a tube by eliminating the joints. In accordance with this embodiment of the invention, an inelastic sack of thermoplastic material is fabricated as an integral part of a longitudinally-extending tube. First, a distal end portion of plastics tubular material is mechanically expanded to form a longitudinally-extending expanded portion. Next, a main body or supporting tube is positioned inside the tubular material. The supporting tube, preferably, has a main body formed from a spring guide and a leading or distal end formed from a fusible, relatively rigid, material. Finally, the distal end of the supporting tube and the end of the expanded portion of the tubular material are heated to shrink and fuse the tip of the tubular material to the supporting tube. A portion of the expanded material is not heated, and forms an inelastic sack or balloon. Since the sack is an integral part of the tubular material, there are no joints connecting the expanded portion to the tubular material.

In a modification of this embodiment, a heatshrinkable elongate tube of material, such as TEFLON (TFE) material, is used to form the dilator. First a longitudinally-extending guide wire is positioned inside the expanded tube. Second, spaced-apart portions, for instance, proximal and distal ends of the tube are heatshrunk to the guide wire. A portion of the tube intermediate the ends is not heated and remains expanded to form a "balloon" or inelastic sack. Third, a plug of inert material, such as TEFLON (FEP or PFA) is inserted into the distal end of the guide. Finally, the plug or tip is heated to effect a bond between the tube and the plug and to seal the distal end of the tube.

Another dilator according to the present invention utilizes mechanical, instead of pneumatic, action to compress the deposits of fatty substances. With this embodiment, a dilator is used having a plurality of longitudinally-extending wires that are buckled radially when a compressive stress or force is imposed on the wires after they have been inserted into an artery. The compressive stress is applied by applying a tensile force to an internal "pull" wire surrounded by the buckling wires and having a distal end attached to distal ends of the wires to be buckled. A spring guide coil has a first portion wrapped around a first or distal end of the buckling wires and a second portion spaced from the first portion. When the tensile force is applied by pulling on the internal pull wire, the wires buckle in the region between the portions encircled by the spring guide coil. Preferably, the wires are pre-buckled or pre-formed so that the buckling occurs in a predetermined region. In a modification of this embodiment, a part or all of the buckling portion of the wires is covered with an elastic membrane. A significant advantage of this embodiment is that blood flow through an artery is not occluded during dilation of the artery.

A third embodiment of the present invention combines the first two embodiments, that is, a thin elastic membrane and wires that can be buckled by a compressive stress. The membrane, which may be made of a material such as silastic, prevents or minimizes possible damage to the intima portion of an artery being dilated. Further, the membrane can be expanded by pneumatic pressure, in conjunction with the mechanical expansion or buckling of the wires, so that more uniform distribution of pressure and radial dilation is obtained.

A fourth embodiment of the present invention utilizes a dilator that has a cannula with a plurality of longitudinally-extending slots formed in its distal end. During insertion of the cannula into an artery, a sleeve encompasses the distal end to prevent its expansion. After the cannula is positioned in a desired location, a translatable member, such as a spherical ball, positioned in front of the distal end of the cannula is pulled rearwardly by a wire, either simultaneously with or after rearward movement of the sleeve. Rearward movement of the ball expands the split distal end portion of the cannula and rearward movement of the dilator dilates the artery. When the split distal end is formed of a relatively rigid material, the degree of dilation can be controlled by the amount of rearward movement of the spherical member.

The invention, and its objects and advantages, will become more apparent in the detailed description of the preferred embodiments hereinafter presented.

BRIEF DESCRIPTION OF THE DRAWINGS

In the detailed description of the preferred embodiments of the invention hereinafter presented, reference is made to the accompanying drawings, in which:

FIG. 1 is a schematic, partial longitudinal cross section of one embodiment of the present invention;

FIG. 2 is a schematic view of the embodiment of FIG. 1 in a compressed position;

FIG. 3 is a schematic, partial longitudinal cross section of another embodiment of the present invention;

FIG. 4 is a view of the embodiment of FIG. 3 in a dilating position;

FIG. 5 is a view taken along line 5—5 of FIG. 3;

FIG. 6 is a schematic view of a modification of the embodiment of FIG. 4 taken along line 6—6 of FIG. 4;

DESCRIPTION OF THE PREFERRED EMBODIMENTS

Figure 7:
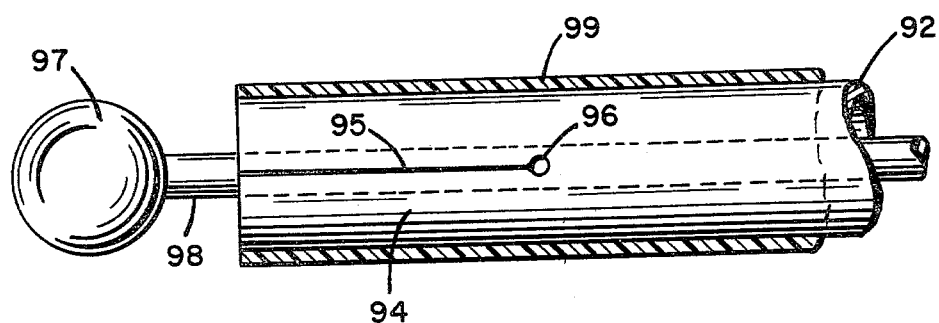
FIG. 7 is a schematic, partial longitudinal cross section of another embodiment of the present invention.

Because surgical dilators are well-known, the present description will be directed in particular to elements forming part of, or cooperating more directly with, the present invention. Elements not specifically shown or described herein are understood to be selectable from those known in the art.

Referring now to the drawings, and to FIGS. 1 and 2 in particular, one embodiment of the present invention is illustrated and will be described in connection with a dilator, generally designated 10. For the purposes of clarity, the portion of the artery encompassing the dilator or dilator assembly of the present invention has been omitted from all of the figures.

The dilator 10 has a longitudinally-extending support member, generally designated 12, positioned inside and encompassed by a longitudinally-extending tubular member, generally designated 13. During a dilation procedure, the components of the support member 12 provide guide means for guiding insertion of the dilator into an artery. The support member 12 has a bipartite distal end portion, generally designated 14, and a proximal end portion that extends outside an artery to be dilated (not shown) when the distal portion 14 is positioned in a desired location in an artery. The end portion 14 includes a relatively rigid end portion 16, formed of Teflon or other fusible suitable material, and a spring wire guide 18 forming a flexible guide member extending from the end portion 16 towards the proximal end of the support means or member. Preferably, the spring wire guide 18 partially encompasses the end portion 16, as illustrated in FIGS. 1 and 2. An annular member 20 is positioned between the end of portion 16 and wire guide 18 in order to form a blocking surface to limit forward movement of the spring wire guide. The annular member, when heated together with a portion of the tubular member 13, melts to fuse tubular members 13 and end portion 16 to each other.

The aforementioned tubular member 13 has an enlarged distal end portion, generally designated 24, and a proximal end portion. The enlarged end portion 24 is formed by expanding the tube mechanically, for instance, by forcing the tube over a heated mandrel. The enlarged end portion 24, after assembly of the dilator 10, has a first part 26 of the side wall of the tube forming an integral, radially protruding, enlarged balloon or inelastic sack, and a second part that is heat shrunk and sealed to annular member 20 and/or end portion 16. During a dilation procedure, the sack portion 26 is expanded into contact with walls of an artery to provide means for dilating the artery.

The dilator 10 is manufactured as follows:
(a) first, a distal end portion of a longitudinally-extending tubular member is mechanically enlarged;
(b) second, a support member having a relatively rigid end portion made of fusible material and a spring wire guide extending rearwardly from the end portion is positioned inside the tubular member with a part of the end portion surrounded by the distal end of the tubular member;
(c) third, the end of the tubular member and at least a part of the end portion of the support member are heated so that the tubular member is heat shrunk and fused to the end portion. The non-heated portion of the tubular member retains the enlarged shape thereby forming an inelastic sack.

The dilator 10 can also be manufactured from an expanded longitudinally-extending tube of heat-shrinkable material. With this method, which is the presently preferred method, the following steps are used:
(a) first, the spring wire guide 18 is positioned inside or enveloped by the expanded tube;
(b) second, distal and proximal end portions of the tube spaced from each other are heated so that the tube shrinks about the wire guide, the non-heated portion between the heated portions maintains its original shape to form an inelastic sack;
(c) third, a plug of material is inserted into the distal end of the wire guide and at least a portion of the plug is enveloped or encompassed by the heat-shrunk tube; and (d) fourth, the plug is heated, for instance to a temperature between approximately 621° and 627° F. to fuse and bond the plug and tube to each other so that the plug seals the distal end of the tube.

In a modification of this method, the plug is positioned inside the wire guide prior to initial heat shrinking of the tube. A problem sometimes arises with this method in that positioning of the plug inside the wire guide can be difficult.

The previously described methods of fabrication eliminate the possibility of leakage from joints or rupture of the joints connecting the inelastic sack to the tubular member by eliminating the joints. The inelastic sack is fabricated as an integral part of the tubular member by expanding the member during manufacture or by expanding the member mechanically. Since the tube is composed of a thermoplastic material, it will revert to, or nearly to, its original shape when sufficient heat is applied (commonly known as "shrink tubing"). To form the balloon or inelastic sack, a portion of the tube where the sack is to be located is not heated.

When it is desired to use dilator 10 to compress fatty substances in an artery, the dilator is inserted into the artery with its distal end located in a desired position using a conventional method. For instance, an incision is made to give access to an artery to be dilated. A guide wire is then inserted through the incision into the artery. Next, a hollow catheter guided on the guide wire is inserted into the artery. The guide wire is then removed and the dilator 10 is inserted through the hollow catheter. Alternatively, if the artery to be dilated has already been cut, for instance during open-heart or bypass surgery, the dilator 10 can be inserted directly into the artery. In the latter case, a shorter dilator 10 is normally used. In either case, the proximal end of the dilator normally remains outside the body. To minimize trauma during insertion, and to minimize the possibility that build-up materials might be broken away from the artery during insertion of the dilator, the interior of the dilator is preferably subjected to reduced pressure, in a known manner, so that the sack portion 26 is contracted towards the axis of tubular member 13. In this manner, the maximum diameter of the tubular member is reduced. Once the dilator is located in a desired position, the reduced pressure is replaced with either atmospheric or a pressure of up to five atmospheres, so that the sack portion 26 expands into contact with the walls of the artery thereby dilating the artery and compressing fatty substances deposited thereon.

As an aid to better understanding this embodiment of the present invention, some representative dimensions will be set forth. It is to be realized that these dimensions are merely illustrative of one embodiment of the present invention. The dilator has an overall length of approximately 145 cm, with an end portion of approximately 3 cm. An annular member of approximately 1.5 cm encompasses the end portion. The distal end of a tubular member is heat shrunk and sealed to the annular member for a distance of approximately 0.5 cm. The heat shrunk portion of the tubular member gradually extends or expands for a distance of between 1 to 2 mm to an enlarged portion having a diameter of between approximately 0.18 cm and 0.32 cm. A spring guide wire fabricated from 0.008 inch diameter wire having an 0.038 inch outside diameter is positioned inside the tubular member. The end portion, which is preferably a Teflon bead, has an outside diameter of approximately 0.020 inch. The annular member is preferably formed of FEP light wall tubing that melts to seal a chamber formed within the sack portion 26 when expanded PTFE tubing forming the tubular member is shrunk at the tip.

Referring now to FIGS. 3 to 5 of the drawings, a dilator according to the present invention, generally designated 40, is illustrated.

The dilator 40 has a longitudinally-extending center, first or pull wire 42 with a distal end 44 connected to a first securing or bulbous member 46 located at the distal end of the dilator, which is generally designated 48. Preferably, member 46 is shaped to facilitate insertion of the dilator 40 into an artery. The proximal end 50 of the wire 42 passes through and extends beyond a second securing, or housing member, generally designated 52. The housing member has a longitudinally-extending and preferably axially-extending, bore 53 for guiding longitudinal movement of the wire 42. A plurality of second longitudinally-extending, or dilating wires, for instance six as illustrated, encompass the pull wire 42. Distal ends 56 of the wires are connected to the first bulbous member 46, and proximal ends 58 are securely held by the second, or housing member 52.

A blocking member 60 is welded or otherwise affixed to the center wire 42 and to the dilating wires 54 a predetermined distance, for instance 1.0 cm, from bulbous member 46. It will be appreciated that the dilating wires 54 can terminate at the member 60 rather than at the member 46. Also, member 60 can be eliminated. A first spring wire guide 62 fabricated from, for instance, 0.004 inch diameter wire, is wrapped around the center wire and dilating wires between the members 46 and 60 thereby forming first encompassing means. A second spring wire guide 64 forming second encompassing means has a distal end 66 positioned a predetermined distance, for instance, between approximately 0.5 and 0.65 cm, from the blocking member 60. If the blocking member is eliminated, the end will be spaced from a facing end of the first spring wire guide. A proximal end 68 of the second spring wire guide 64 extends inside the housing 52 and is secured with the dilating wires by heat shrinking of the housing member 52, or other suitable means.

Considering now the housing member 52, it has an insert 70 positioned inside and held by a tubular member 72. Preferably, the insert 70 has a plurality of longitudinally-extending grooves 74 for receiving the proximal ends 58 of the dilating wires 54. The length of the grooves is sufficiently long, for instance approximately 1.0 cm, to ensure that the proximal ends 58 are frictionally held between facing surfaces of the insert 70 and the tubular member 72. Such contact can be enhanced by engagement of an innermost end 76 of insert 70 with curved portions 78 of the wires 54. It will be appreciated that the grooves 74 can be replaced with or cooperate with corresponding grooves formed in inner surfaces of tubular member 72. As illustrated in phantom lines in FIG. 4, a compressive sleeve 82 can be applied to tubular member 72 to clamp together the components of housing 52.

As previously mentioned, the length of the grooves 74 in one embodiment is approximately 1.0 cm. With this embodiment, the overall length of the insert 70 is approximately 1.5 cm, and the overall length of the housing member 52 is approximately 4.0 cm. Other representative dimensions include a bore diameter 53 between approximately 0.02 and 0.036 cm; and an insert 70 having a maximum outer diameter of between approximately 0.8 and 0.12 cm and a minimum diameter (between the bottoms of two radially aligned grooves) of between approximately 0.06 and 0.092 cm. A suitable spring guide 64 is fabricated from 0.004 inch diameter wire and has an outer diameter between approximately 0.038 and 0.045 inches (0.096 and 0.114 cm). Suitable dilating wires 54 are fabricated from 304 stainless or beryllium copper having a diameter of between approximately 0.008 and 0.012 inches (0.020 to 0.030 cm). It will be appreciated that the diameter of the dilating wires 54 determines the depth of the grooves 74. Also, the buckling strength of wires 54, taken as a group, must be less than the tensile strength of pull wire 42, so that the wires 54 buckle instead of wire 42 breaking.

Referring now to FIG. 6, a modification of the embodiment of FIGS. 4 and 5 is illustrated. Since this embodiment is similar to the embodiment of FIGS. 4 and 5, the same reference numerals, with primes attached, have been used to identify the same or similar components.

FIG. 6 illustrates a dilator, generally designated 40' having a plurality of dilating wires 54' surrounding a pull wire 42'. A first spring guide (not shown) encompasses a distal end portion of the dilating wires and the pull wire. A second spring guide (not shown) is spaced from the first spring guide and extends to the proximal end of the dilator. The region between the two spring guides forms a buckling region for the dilating wires 54'. In the embodiment of the present invention illustrated in FIG. 6, the dilating wires are encompassed by a thin elastic membrane 80, formed of a material such as silastic, that stretches when the wires 54' are buckled. The membrane 80 prevents or minimizes possible damage to the intima of an artery being dilated. Since the membrane encompasses only a portion of the wires 54', the membrane does not interfere with flow of blood through the dilator 40'.

In another embodiment of the present invention (not illustrated), a membrane similar to membrane 80 is shaped like the tubular member 13 illustrated in FIGS. 1 and 2. With this embodiment, the membrane or tubular member is pneumatically expanded, while the dilating wires are mechanically buckled. The combination of pneumatic and mechanical expansion provides a more uniform distribution of pressure and radial dilation.

In the embodiment illustrated in FIG. 6, the peripheral surfaces of adjacent dilating wires contact each other to form a generally tubular member encompassing the pull wire.

However, it is within the scope of the present invention to space adjacent peripheral surfaces apart from each other, or to have some surfaces contacting and some spaced apart from each other.

Since the embodiments illustrated in FIGS. 3 to 6 all function in generally the same manner, only the functioning or use of the embodiment of FIG. 3 will be explained.

In use, the dilator 40 is inserted into an artery to be dilated by a standard surgical procedure, for instance, one of the procedures previously described in connection with use of dilator 10. The buckling region of the dilator 40, i.e., the region between facing ends of the two spring wire guides 62 and 64, is positioned in or just past the portion of the artery to be dilated. Next, the housing 52 is grasped to prevent its movement, and the proximal end 50 of wire 42 is moved rearwardly (to the right as illustrated). Since the proximal ends of the pull wire and dilating wires are interconnected, and since rearward movement of the dilating wires is prevented by housing 52, rearward movement or a tensile force on pull wire 42 places a compressive force on the dilating wires 54. Since longitudinal movement of the wires is prevented by housing 52, the wires buckle in the region between the two spring guides. This buckling results in lateral expansion and radial protrusion of the wires and dilation of the artery. Thus, movement of the first wire 42 radially outwardly deforms portions of the second wires 54. Preferably, to better control the buckling of the wires, the wires are prebuckled in the region between the two spring guides.

Figure 8:
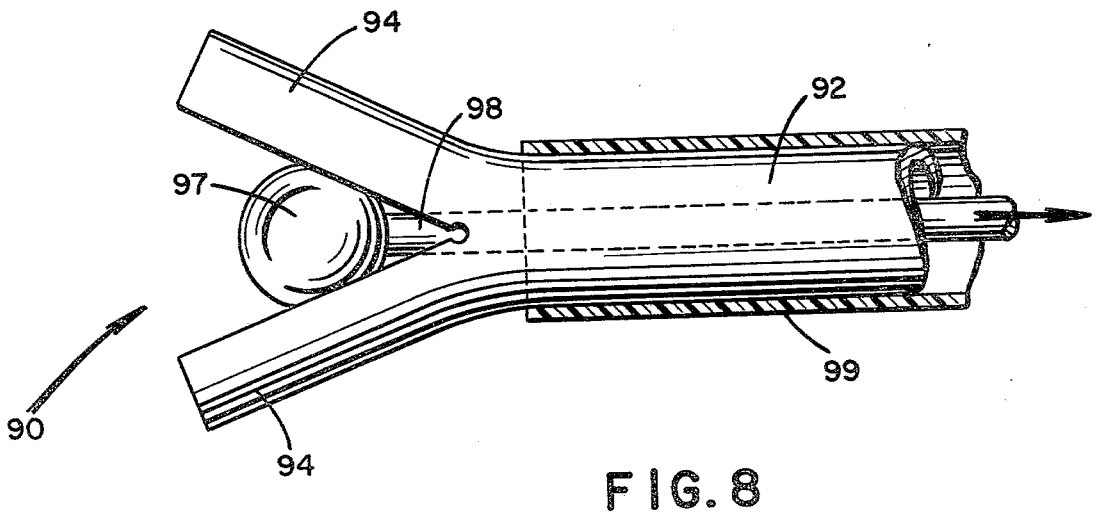
FIG. 8 is a view of the embodiment of FIG. 7 in a dilating position.

Referring now to FIGS. 7 and 8, another embodiment of a dilator according to the present invention, which is generally designated 90, is illustrated.

The dilator 90 has a longitudinally-extending tubular member 92 with a distal end portion 94 formed with at least two slits 95 that extend from the distal end to one or more openings or apertures 96 formed in side walls of the tubular member. The openings 96 are provided to minimize stress concentration at the end of the slits 95. The length of the slits 95 is preferably approximately twice the diameter of the tubular member. An expansion member, such as a spherical ball 97, is located at the distal end of the tubular member. Preferably, the diameter of the ball is equal to or slightly larger than the diameter of the tube so that the ball is not forced into the tube when the dilator 90 is inserted into an artery. A wire 98 has a distal end rigidly connected to the ball, for instance by welding, and a proximal end (not shown) extending from the proximal end (not shown) of the tubular member 92. A longitudinally-extending sheath 99 encompasses the tubular member 92 to prevent inadvertent opening of the slit end during insertion of the dilator. Preferably, at least the distal end portion of the tubular member 92 is relatively rigid, so that movement of the ball expands the slit end, as illustrated in FIG. 8.

In use, the dilator of this embodiment of the present invention is inserted in a conventional manner into an artery to be dilated. The distal end 94 of the dilator 90 is positioned past the portion of the artery to be dilated. The proximal end of the dilator remains outside of the artery or body with the proximal end of the wire 98 extending beyond the ends of the tubular member 92 and sheath 99. In order to start a dilation, the sheath and wire are moved to the right, as illustrated in FIG. 8, so that the ball 97 enters the split end and forces it open. Subsequent rearward movement of the dilator assembly 90 dilates the occluded portion of the artery.

In one embodiment of the present invention, the proximal ends of the sheath and wire are interconnected so that the movement is conjoint. In another embodiment, the proximal ends are separated from each other, so that the sheath must be moved before the wire is pulled. It will be appreciated that the radial distance between the radially protruding split ends of the tubular member is a function of the amount of movement of ball 97 by wire 98.

The embodiment illustrated in FIGS. 7 and 8 is formed with two longitudinally-extending slits 95. It will be appreciated that more than two such slits can be formed to obtain more uniform compression of the occluded portion of the artery. Also, although not illustrated in FIGS. 7 and 8, it will be appreciated that a spring wire guide can be positioned at the distal end of the ball 97 to facilitate insertion of the dilator 90 into an artery. Also, when the tubular member 92 is formed of relatively rigid material, the sheath can be eliminated.

Previously, specific embodiments of the present invention have been described. It should be appreciated, however, that these embodiments have been described for the purposes of illustration only, without any intention of limiting the scope of the present invention. Rather, it is the intention that the present invention be limited only by the appended claims.

What is claimed is:

1. A dilator for dilating arteries to compress fatty substances deposited on the walls and in the lumens of the arteries, the dilator comprising:

a longitudinally-extending tubular member having wall means extending between a leading distal end and a trailing proximal end, the length of the wall means being such that the proximal end is positioned outside of the artery during a dilation procedure, the wall means including an integral, radially enlarged protruding portion which is integral with the wall means and forms a single piece therewith and a continuation thereof closely spaced rearwardly from the distal end, said protruding portion forming means for dilating an artery; and guide means for guiding insertion of the dilator into an artery, the guide means including a longitudinally-extending flexible member positioned inside and extending the length of said tubular member and having a distal end connected to said tubular member, forwardly of the protruding portion, said longitudinally-extending flexible member extending the length of the tubular member as a flexible spring.

2. A dilator according to claim 1, wherein said guide means includes a relatively rigid member connected to said flexible member and forming the distal end of the dilator, the distal end of said tubular member being sealed to said relatively rigid member.

3. A dilator according to claim 1, wherein said distal end of said guide means is sealed, and wherein a proximal end of said tubular member is selectively connectable to a source of vacuum and pressure.

4. A dilator according to claim 1, wherein said tubular member has a sealed distal end so that vacuum can be applied to said tubular member to contract the protruding portion toward an axis of the tubular member.

* * * * *